US011278852B2

(12) United States Patent
Han et al.

(10) Patent No.: US 11,278,852 B2
(45) Date of Patent: Mar. 22, 2022

(54) APPARATUS FOR MANUFACTURING COSMETIC

(71) Applicant: Amorepacific Corporation, Seoul (KR)

(72) Inventors: Kyung Sup Han, Yongin-si (KR); Jin Nam, Yongin-si (KR); Won Seok Park, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 257 days.

(21) Appl. No.: 16/729,873

(22) Filed: Dec. 30, 2019

(65) Prior Publication Data
US 2020/0206699 A1 Jul. 2, 2020

(30) Foreign Application Priority Data

Dec. 31, 2018 (KR) .................. 10-2018-0174275

(51) Int. Cl.
*B01F 3/08* (2006.01)
*A45D 34/00* (2006.01)
(Continued)

(52) U.S. Cl.
CPC ............. *B01F 3/088* (2013.01); *A45D 34/00* (2013.01); *A45D 40/24* (2013.01); *A61K 8/062* (2013.01);
(Continued)

(58) Field of Classification Search
CPC . A61K 8/062; A61K 8/064; B01F 2215/0031; B01F 3/0807; B01F 13/0022; B01F 13/0059; B01F 13/0084; B01F 15/0087; B01F 2003/0849; B01F 3/0865; B01F 3/088; B01F 5/0065; B01F 5/0496; B01F 5/0647; B01F 5/0652;
(Continued)

(56) References Cited

U.S. PATENT DOCUMENTS 4,773,562 A * 9/1988 Gueret .................. A45D 40/24
222/135
5,169,029 A * 12/1992 Behar ................. B05B 11/3084
128/200.23
(Continued)

FOREIGN PATENT DOCUMENTS

DE            199 11 776 A1    9/2000
DE    10 2008 001 312 B4       3/2015
(Continued)

*Primary Examiner* — Tony G Soohoo
(74) *Attorney, Agent, or Firm* — Sughrue Mion, PLLC

(57) ABSTRACT

Provided according to an aspect of the invention may be an apparatus for manufacturing cosmetic, which includes a housing which forms an outer appearance; an internal phase container which is provided in the housing, and which stores internal phase fluid excluding surfactant; an external phase container which is provided in the housing, and which stores external phase fluid excluding surfactant; a channel unit which generates emulsion by mixing the internal phase fluid provided from the internal phase container and the external fluid provided from the external phase container; and an operative unit which provides external force required to form and discharge emulsion at the channel unit by manipulation of a user.

16 Claims, 7 Drawing Sheets

(51) Int. Cl.
*A61K 8/06* (2006.01)
*B01F 5/00* (2006.01)
*B01F 5/04* (2006.01)
*B01F 5/06* (2006.01)
*B01F 15/00* (2006.01)
*A45D 40/24* (2006.01)

(52) U.S. Cl.
CPC ............ *A61K 8/064* (2013.01); *B01F 3/0807* (2013.01); *B01F 3/0865* (2013.01); *B01F 5/0065* (2013.01); *B01F 5/0496* (2013.01); *B01F 5/0647* (2013.01); *B01F 5/0652* (2013.01); *B01F 15/0087* (2013.01); *A45D 2034/005* (2013.01); *A45D 2200/056* (2013.01); *A45D 2200/058* (2013.01); *B01F 2003/0849* (2013.01); *B01F 2215/0031* (2013.01)

(58) Field of Classification Search
CPC ............ B01F 11/3074; B01F 11/3084; A45D 2034/005; A45D 2200/056; A45D 2200/058; A45D 34/00; A45D 40/24
See application file for complete search history.

(56) References Cited

U.S. PATENT DOCUMENTS

| | | | |
|---|---|---|---|
| 6,817,753 B2* | 11/2004 | Buenger | B65D 83/68 222/145.5 |
| 9,655,431 B2* | 5/2017 | Ham | A45D 40/00 |
| 9,789,504 B2* | 10/2017 | Quennessen | B05B 11/3083 |
| 9,839,931 B2* | 12/2017 | Burrowes | B05B 11/3084 |
| 2018/0126400 A1* | 5/2018 | Burrowes | B05B 1/341 |
| 2019/0038525 A1* | 2/2019 | Konno | B65D 83/62 |
| 2020/0205545 A1* | 7/2020 | Han | B01F 13/0059 |
| 2020/0206699 A1* | 7/2020 | Han | B01F 13/0059 |
| 2020/0376449 A1* | 12/2020 | Han | B01F 3/0807 |
| 2020/0397696 A1* | 12/2020 | Panagiotou | A61K 47/12 |

FOREIGN PATENT DOCUMENTS

| | | | | |
|---|---|---|---|---|
| DE | 10 2014 017 032 A1 | 5/2016 | | |
| FR | 2 669 243 A1 | 5/1992 | | |
| KR | 1020180036624 A | 4/2018 | | |
| KR | 1020180108235 A | 10/2018 | | |
| WO | 2018/174694 A1 | 9/2018 | | |
| WO | WO-2018174693 A1 * | 9/2018 | | |
| WO | WO-2018174694 A1 * | 9/2018 | ............... | B01F 5/00 |

* cited by examiner

[FIG. 1]
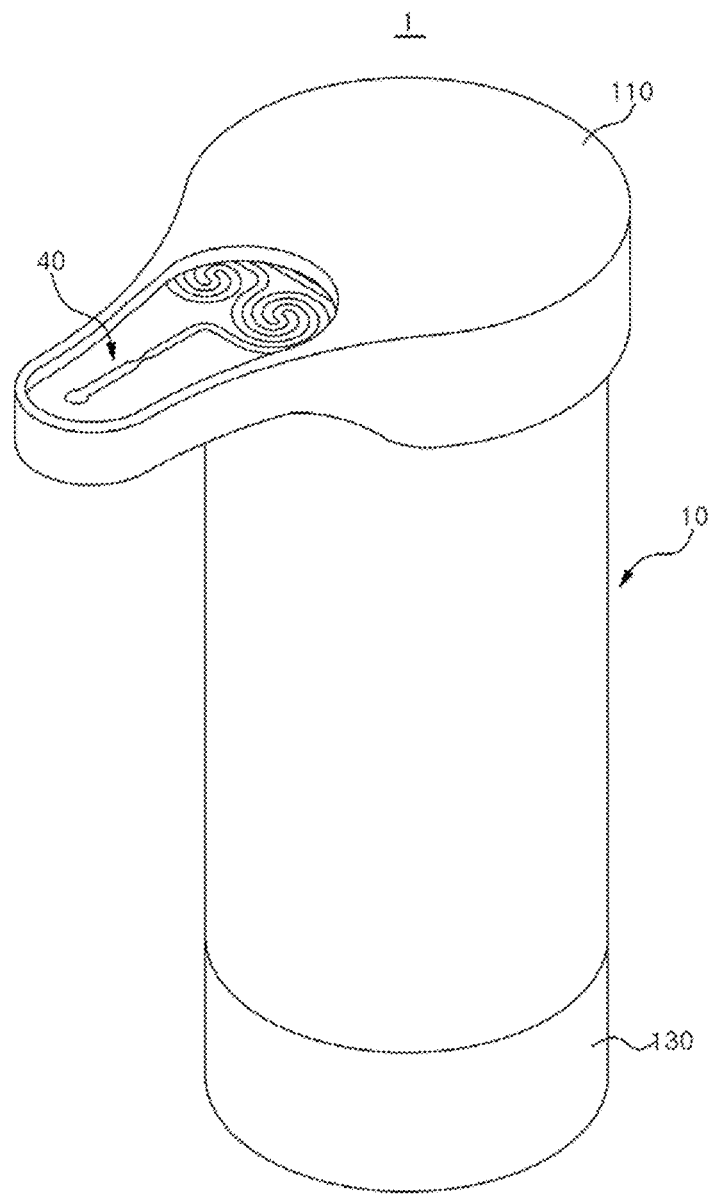

[FIG. 2]
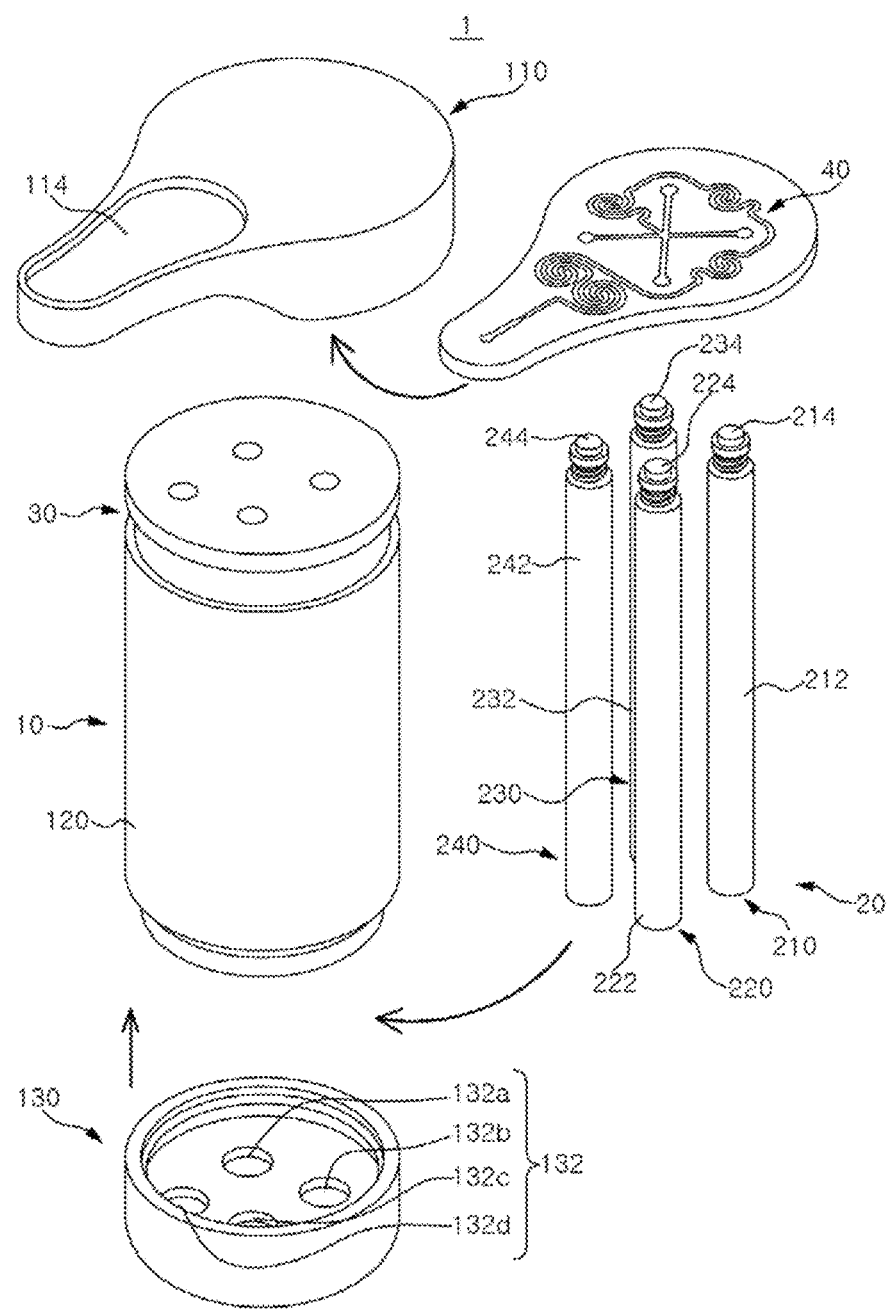

[FIG. 3]
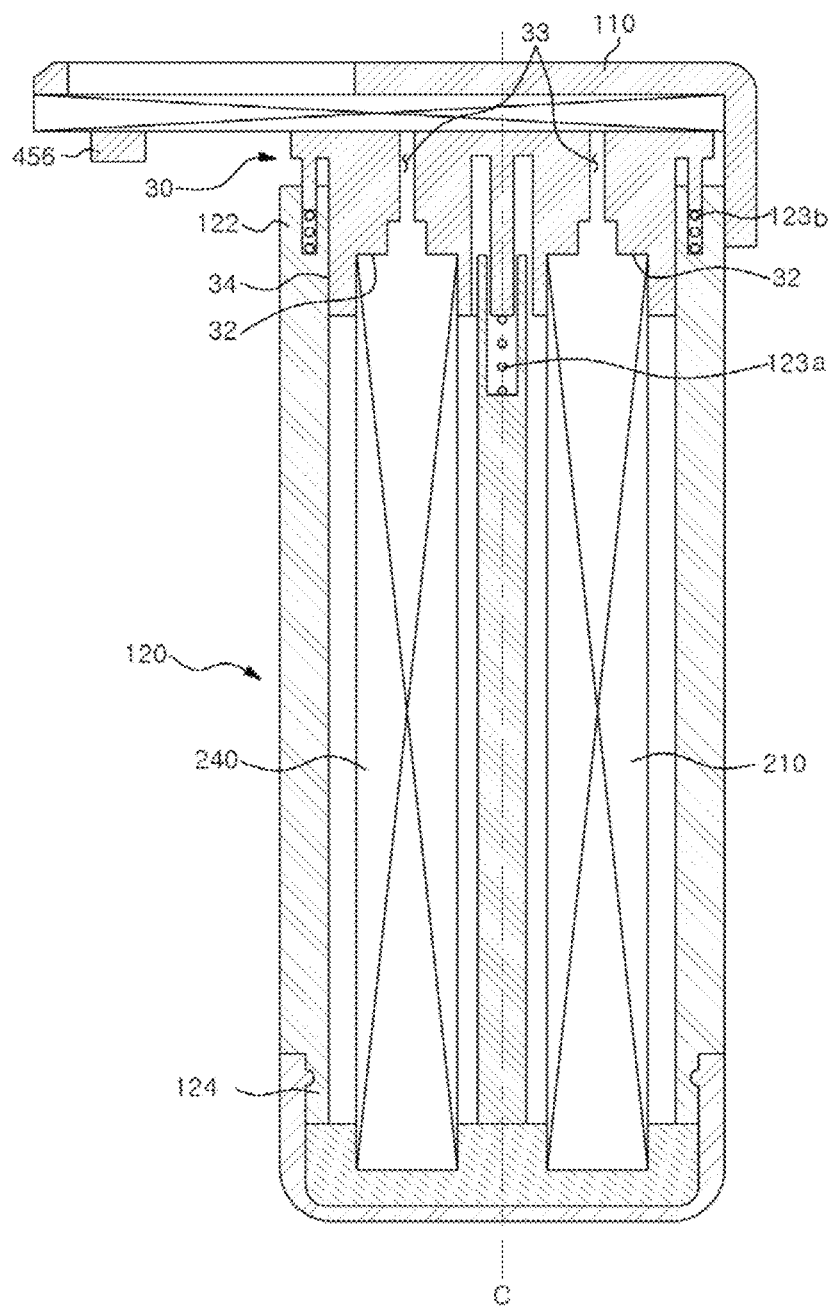

[FIG. 4]
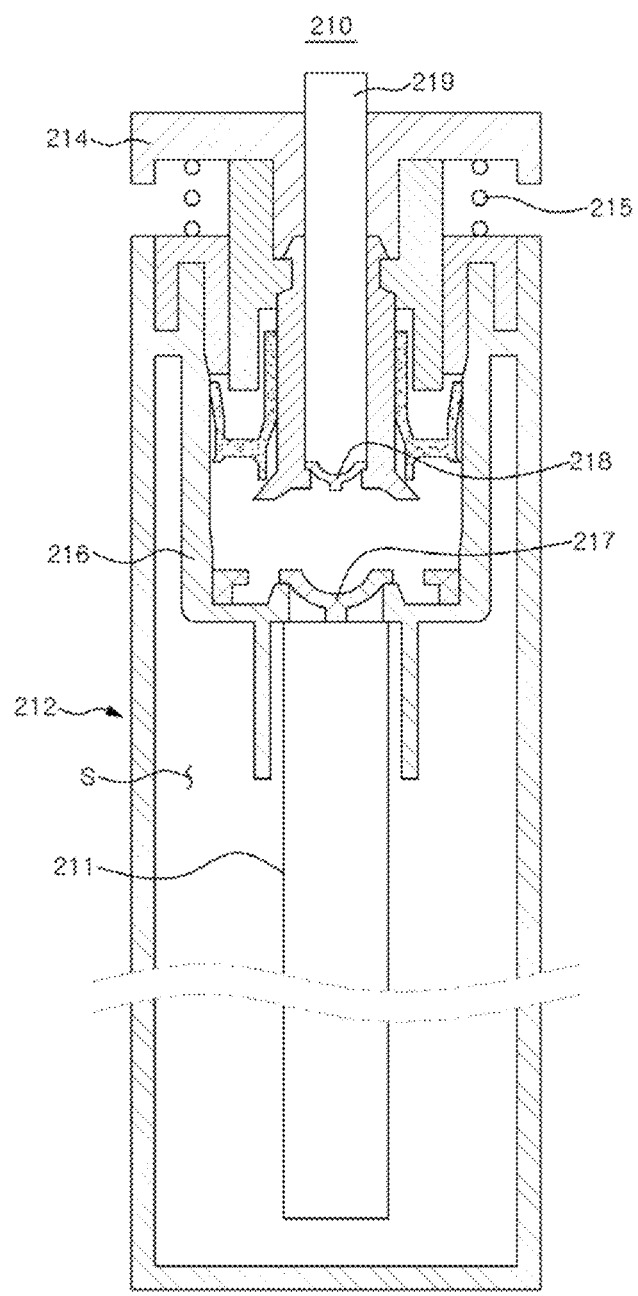

[FIG. 5]
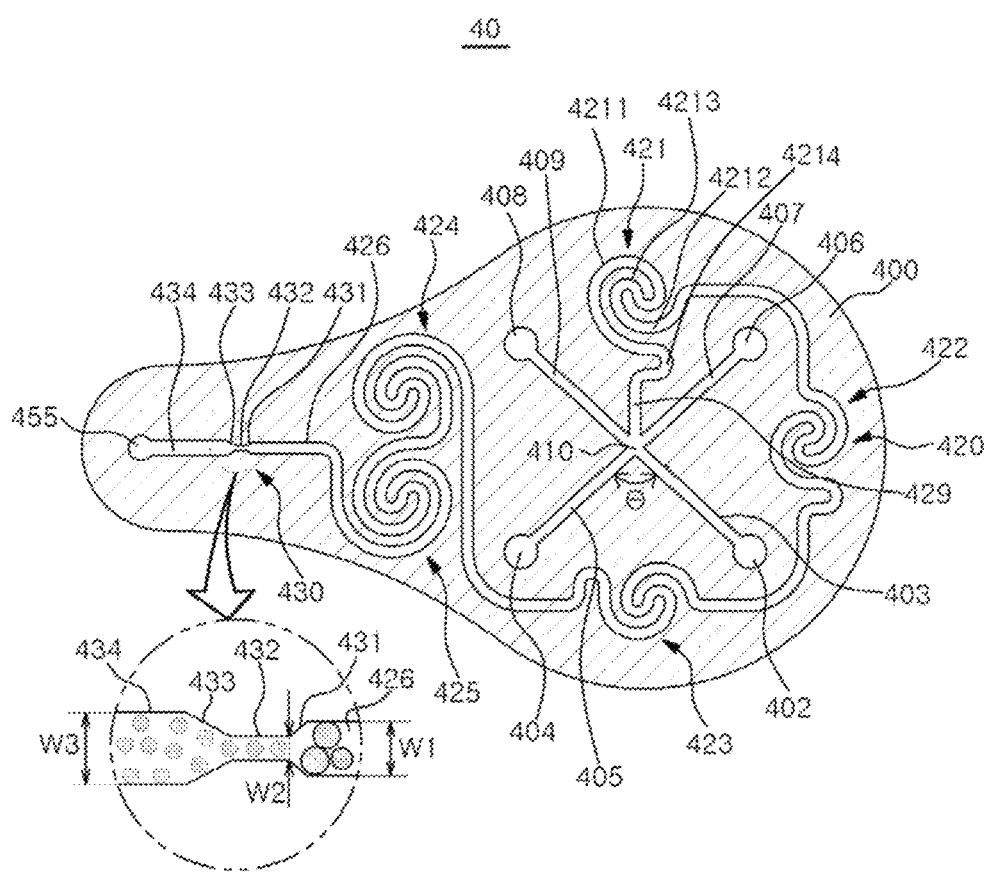

[FIG. 6]
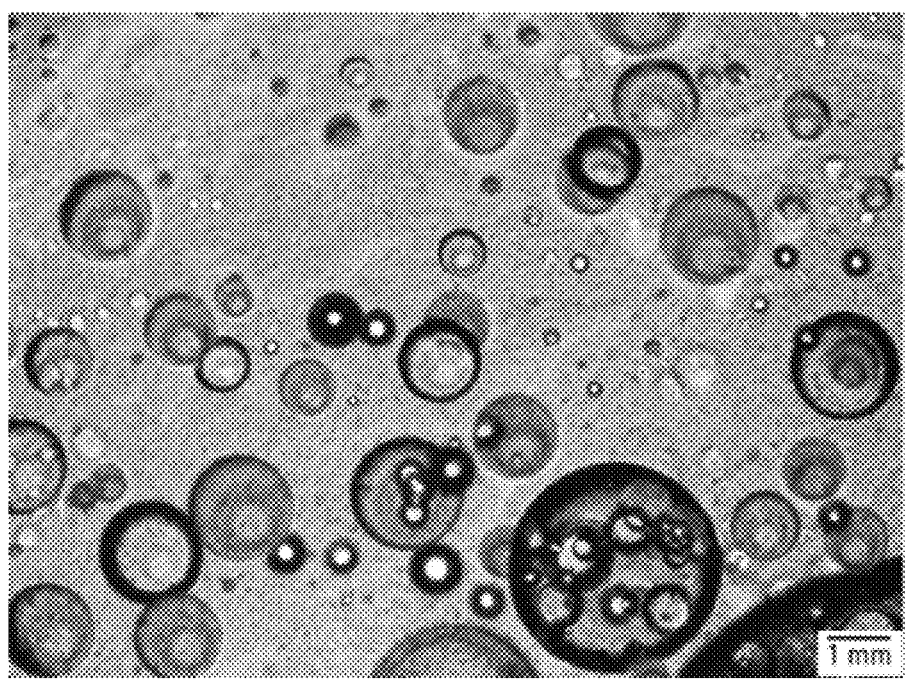

[FIG. 7]
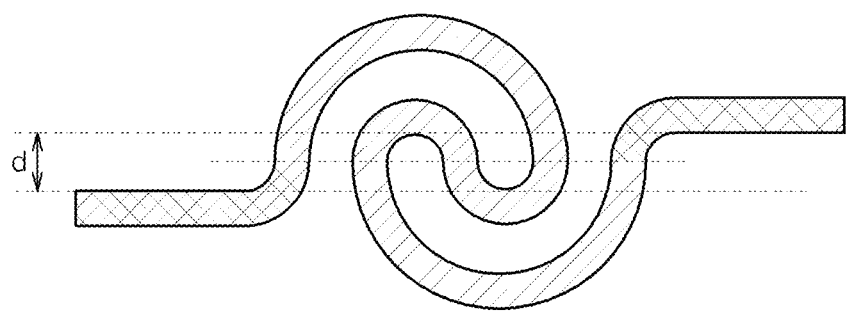

APPARATUS FOR MANUFACTURING COSMETIC

CROSS-REFERENCES TO RELATED APPLICATION

This application is based on and claims priority of Korean Patent Application No. 10-2018-0174275, filed on Dec. 31, 2018 with the Korean Intellectual Property Office, the entire contents of which are hereby incorporated by reference.

TECHNICAL FIELD

The disclosure relates to an apparatus for manufacturing cosmetic.

BACKGROUND

Fluid emulsification means that one liquid of two fluids which are not mixed with each other like water and oil is dispersed in the form of small particles to be stably disposed within the other liquid. Such emulsification technology is widely used in the manufacture field of cosmetics, such as lotion, cream, essence, massage cream, cleansing cream, make-up base, foundation, eyeliner, mascara or the like.

Specifically, cosmetic may include O/W (Oil in Water) emulsion which is manufactured by dispersing hydrophobic fluid, such as oil, uniformly in a small particle state in hydrophilic fluid, such as water, or W/O (water in oil) emulsion which is manufactured by dispersing hydrophilic fluid uniformly in a small particle state in hydrophobic fluid.

In a cosmetic manufacture process during which such emulsion is produced, surfactant was used in order to emulsify two fluids which are not easily mixed. The surfactant is a chemical material having no close relation to true function of cosmetic. Nowadays, customers show a tendency not to prefer additives, such as surfactant, which have no close relation to functions of cosmetic. Hence, several methods for manufacturing cosmetic, in which surfactant is not used, have been suggested.

For example, a method in which special raw material (hydrophilic polymer, silicone polymer) is added to emulsion, or a method in which special procedure (pickering, capsulation, coacervation, Layer-By-Layer) or special facility (high frequency focused ultrasound) is used has ever been suggested as a method for manufacturing cosmetic without using surfactant.

However, in such a case where special raw material is added, or special procedure or facility is used, there is a drawback that manufacture process becomes complex and production cost becomes higher.

SUMMARY

Exemplary embodiments of the invention, which have been conceived to address above-described problems, provide an apparatus for manufacturing cosmetic that is capable of manufacturing cosmetic into which no surfactant is added.

Further, exemplary embodiments of the invention provide an apparatus for manufacturing cosmetic, which is capable of satisfying customer's desire for fresh cosmetics.

Further, exemplary embodiments of the invention provide an apparatus for manufacturing cosmetic that is capable of manufacturing cosmetic, at a low production cost, into which no surfactant is added.

According to an aspect of the present invention, there is provided an apparatus for manufacturing cosmetic, the apparatus comprising: a housing which forms an outer appearance; an internal phase container which is provided in the housing, and which stores internal phase fluid excluding surfactant; an external phase container which is provided in the housing, and which stores external phase fluid excluding surfactant; a channel unit which generates emulsion by mixing the internal phase fluid provided from the internal phase container and the external phase fluid provided from the external phase container; and an operative unit which provides external force required to form and discharge emulsion at the channel unit by manipulation of a user, wherein by operation of the operative unit, more amount of the external phase fluid is supplied to the channel unit than the internal phase fluid, and wherein the channel unit includes: an internal phase fluid injection hole to which the internal phase fluid is provided from the internal phase container; an external phase fluid injection hole to which the external phase fluid is provided from the external phase container; a confluence part in which the internal phase fluid provided from the internal phase fluid injection hole and the external phase fluid provided from the external phase fluid injection hole are mixed with each other; and a mixing section including a plurality of mixing parts which extend from the confluence part, and which generate emulsion particles by converting proceeding direction of fluid and thus forming vortices in flow.

Further, there is provided an apparatus for manufacturing cosmetic, wherein the respective internal phase container and the external phase container are provided one or more in number, and the channel unit is provided with introducing parts to which fluids from the internal phase container and the external phase container flow, and wherein the fluids which have flown to the introducing parts are guided to the confluence part to be mixed with each other.

Further, there is provided an apparatus for manufacturing cosmetic, wherein by one-time operation of the operative unit, total discharging amount of the external phase fluid discharged from the external phase container is greater than total discharging amount of the internal phase fluid discharged from the internal phase container.

Further, there is provided an apparatus for manufacturing cosmetic, the apparatus further comprising: a functional container which is provided in the housing, and which stores functional fluid, wherein the channel unit includes a functional fluid injection hole to which the functional fluid is introduced from the functional container, and the functional fluid which has flown to the functional fluid injection hole is guided to the confluence part to be mixed with the internal phase fluid and the external phase fluid.

Further, there is provided an apparatus for manufacturing cosmetic, wherein the plurality of mixing parts is disposed around the confluence part with the confluence part as a center.

Further, there is provided an apparatus for manufacturing cosmetic, wherein the channel unit is formed in one or more plates, and the confluence part and the mixing section are provided in a continuous single layer path.

Further, there is provided an apparatus for manufacturing cosmetic, wherein the channel unit is formed in the plate of a single planar panel shape, and the confluence part and the mixing section are located on same planar surface in the plate.

Further, there is provided an apparatus for manufacturing cosmetic, wherein the mixing part includes: a first turning path which guides an entering fluid to be rotated in one direction; a second turning path which guides the fluid rotating in one direction to be rotated in another direction; and a direction converting path which changes a rotational direction of fluid between the first turning path and the second turning path.

Further, there is provided an apparatus for manufacturing cosmetic, wherein the mixing part further includes a vortex prompting path for prompting formation of vortices at upstream of the first turning path or downstream of the second turning path.

Further, there is provided an apparatus for manufacturing cosmetic, wherein the mixing part is provided three or more in number.

Further, there is provided an apparatus for manufacturing cosmetic, wherein the mixing section includes: a first mixing part which is connected to the confluence part; a third mixing part which is located opposite to the first mixing part with respect to the confluence part; and a second mixing part which is located between the first mixing part and the third mixing part.

Further, there is provided an apparatus for manufacturing cosmetic, wherein the mixing section includes a fourth mixing part and a fifth mixing part which are located opposite to the second mixing part with respect to an imaginary straight line passing through the first mixing part, the third mixing part and the confluence part.

Further, there is provided an apparatus for manufacturing cosmetic, wherein the channel unit further includes a particle size adjusting part which reduces size of the emulsion particle included in fluid provided from the mixing section.

Further, there is provided an apparatus for manufacturing cosmetic, wherein the particle size adjusting part includes a convergence maintaining portion which has a width less than that of the mixing flow path of the mixing section.

Further, there is provided an apparatus for manufacturing cosmetic, wherein the particle size adjusting part includes a divergence maintaining portion which is disposed at a rear end of the convergence maintaining portion, and which has a width greater than that of the mixing flow path of the mixing section.

Further, there is provided an apparatus for manufacturing cosmetic, wherein the discharging part which discharges the emulsion is directly connected to a discharging hole formed in the channel unit.

An apparatus for manufacturing cosmetic according to examples of the invention has an advantage that cosmetic can be manufactured without adding surfactant thereto.

Further, it has a beneficial effect of being capable of manufacturing cosmetic using instantaneous emulsification, which can satisfy customer's desire for fresh cosmetics.

Further, there is an advantage that cosmetic to which no surfactant is added can be manufactured at a low production cost.

BRIEF DESCRIPTION OF THE DRAWINGS

FIG. 1 is a schematic perspective view showing a configuration of an apparatus for manufacturing cosmetic according to an embodiment of the present invention.

FIG. 2 is an exploded perspective view of FIG. 1.

FIG. 3 is a cross sectional view of FIG. 1.

FIG. 4 is a cross sectional view of a container of FIG. 2.

FIG. 5 is a cross sectional view showing a channel unit of FIG. 2.

FIG. 6 is a micrograph showing an emulsion particle of an emulsion composition manufactured using the apparatus for manufacturing cosmetic of FIG. 1.

FIG. 7 is a conceptual diagram for designing a vortex promoting path of FIG. 1.

DETAILED DESCRIPTION

Hereinafter, specific exemplary embodiments of the invention will be described in detail with reference to the drawings. Additionally, it is noted that when describing the invention, the detailed description for known configurations or functions may be omitted herein so as not to obscure essential points of the disclosure.

FIG. 1 is a schematic perspective view showing a configuration of an apparatus for manufacturing cosmetic according to an embodiment of the present invention, FIG. 2 is an exploded perspective view of FIG. 1, FIG. 3 is a cross sectional view of FIG. 1, FIG. 4 is a cross sectional view of a container of FIG. 2, and FIG. 5 is a cross sectional view showing a channel unit of FIG. 2.

Referring to FIGS. 1 to 5, an apparatus 1 for manufacturing cosmetic according to an embodiment of the present invention may mix and instantly emulsify fluids stored in a plurality of containers. Herein, the "instantaneous emulsification" may be understood as emulsifying an internal phase fluid into an external phase fluid within a few seconds, and maintaining the emulsified state for a predetermined period of time. That is, the apparatus 1 for manufacturing cosmetic according to an embodiment of the invention may be an apparatus which instantly emulsifies a plurality of raw materials within a few seconds, and supplies it to a user at once.

Further, the apparatus 1 for manufacturing cosmetic may form an O/W emulsion or a W/O emulsion according to a mixing ratio of fluids stored in a plurality of containers. For example, if fluids to be mixed are an oil-based fluid and a water-based fluid, and they are mixed at such a mixing ratio that the amount of the water-based fluid is more than that of the oil-based fluid, the O/W emulsion can be produced. In an opposite case, the W/O emulsion can be produced.

Specifically, the apparatus 1 for manufacturing cosmetic according to an embodiment of the invention may include a housing 10 which forms its outer appearance, a plurality of containers 20 which are provided inside the housing 10 and store at least two different fluids from each other, a channel unit 40 which provides a space where the fluids discharged from the plurality of containers 20 are mixed with each other, and an operative unit 30 which provides pressure for discharging the emulsion produced in the channel unit 40.

In the embodiment, the operative unit 30 is described by way of example as pressing the plurality of containers 20 at the same time to activate pumping units provided in the containers 20. However, the technical idea of the invention is not limited to this. Further, in the embodiment, the activation of the operative unit 30 produces pressure, which enables the discharge of the fluids from the containers 20 to the channel unit 40 and the discharge of the emulsion from the channel unit 40 to the outside. However, the technical idea of the invention is not limited to this, and according to an embodiment, the operative unit 30 may be provided with a configuration for discharging the fluid from the container 20 to the channel unit 40, and a configuration for discharging the emulsion from the channel unit 40 to the outside, separately. In a case where the single operative unit 30 activates the pumping units provided in the plurality of containers 20 at the same time as in the embodiment, the convenience for use can be improved, and it becomes easy to design the channel unit 40.

The housing 10 may be formed in a predetermined shape which accommodates the plurality of containers 20, and the housing 10 is described by way of example as being formed in a cylindrical shape in the embodiment. However, the housing 10 may have a rectangular parallelepiped shape, and there is no limit to its shape.

The housing 10 may include a lid 110 which covers a portion of the channel unit 40 to be described later, a main body 120 which accommodates the containers 20 therein, and a supporting part 130 which supports a bottom side of the container 20.

The lid 110, which surrounds a portion of the channel unit 40, may be formed with a transparent material so that a user can see the fluid flowing in the channel unit 40. Further, an upper portion of the lid 110 may include an opening 114, so that the user can see a portion or whole of the channel unit 40. For example, the opening 114 may be a circular or rectangular hole. However, there is no limit in its shape. The provision of the opening 114 enables a user to confirm emulsification with the naked eye, so reliability for a product can be improved.

Further, the main body 120 may include a neck part 122 which is coupled with the operative unit 30, and an insertion part 124 which is formed opposite to the neck part 122 to be coupled with the supporting part 130, and which provides a space through which the container 20 can be inserted.

The supporting part 130 may be removably coupled with the insertion part 124 for substitution of the container 20, and may support a lower part of the container 20 when being coupled therewith, so that the container 20 can be stably fixed in the housing 10.

The supporting part 130 may include a plurality of grooves 132 for fixing each of the containers 20 which have been installed in the housing 10. The plurality of grooves 132 may be formed having such a depth as to stably support containers 20. Further, the plurality of grooves 132 formed in the supporting part 130 may correspond to the number and the locations of the containers 20.

The containers 20 include an internal phase container storing an internal phase fluid, and an external phase container storing an external phase fluid. For example, the containers 20 may include a first container 210 storing an internal phase fluid, and a second container 220 storing an external phase fluid. In the embodiment, the containers 20 are described by way of example as being four, but the number of the containers is not limited as long as there are provided a container which can store an internal phase fluid independently, and a container which can store an external phase fluid independently. Herein, the container 20 may be detachable to the housing 10, and may be configured such that the container 20 can be refilled with a fluid or a fluid inside the container can be substituted with another. For example, the container 20 may be a cartridge.

In the embodiment, the type of emulsion (e.g., W/O emulsion or O/W emulsion) may be determined according to a ratio at which a plurality of fluids is supplied to the channel unit 40. And, the ratio at which fluids are supplied to the channel unit 40 may be adjusted by the number or the discharging amount of the containers 20 supplying the corresponding fluids. For example, in a case where oil and water are supplied to the channel unit 40, if the supply amount of oil is greater than that of water, W/O emulsion will be produced, while, if the supply amount of water is greater than that of oil, O/W emulsion will be produced.

The plurality of containers 20 may be provided in such a combination as to form an internal phase fluid and an external phase fluid at the time of instantaneous emulsification in the channel unit 40. In the embodiment, the two containers are described by way of example as storing an external phase fluid, so that more amount of external phase fluid can be supplied to the channel unit 40. According to an embodiment, a single container which can discharge relatively more amount may be provided as the second container 220, and in this case, only the single container may be used as a container storing an external phase fluid.

In the embodiment, the apparatus 1 for manufacturing cosmetic may include the first container 210 storing an internal phase fluid, the second container 220 storing an external phase fluid, a third container 230 storing a functional fluid, and a fourth container 240 storing another external phase fluid. The embodiment is described by way of example as oil being used as the internal phase fluid and water being used as the external phase fluid, and thus the first container 210 may store an oil-based fluid, the second container 220 and the fourth container 230, which can be selectively provided, may store a water-based fluid. In this case, the first container 210 may be understood as an internal phase container as it stores an internal phase fluid, and the second container 220 and the fourth container 240 may be understood as an external phase container as they store an external phase fluid. Further, it can be understood that the amount of the external phase fluid supplied to the channel unit 40 from the external phase container is greater than that of the internal phase fluid supplied to the channel unit 40 from the internal phase fluid. For this, the number of the internal phase containers and the number of the external phase containers may be adjusted according to an embodiment. Additionally, the third container 230 may be understood as a functional container as it stores a functional fluid.

When the oil-based fluid and the water-based fluid are discharged at a ratio of 1:2 to be emulsified in the channel unit 40, an O/W emulsion can be formed. Herein, discharging amounts of the pumping units to be described later may be set to be equal to each other, so that each container can discharge the same amount of fluid.

In contrast to this, when the first container 210 stores a water-based fluid, and the second container 220 and the fourth container 240, which is provided selectively, store an oil-based fluid, a W/O emulsion can be produced.

Meanwhile, the third container 230 storing a functional fluid may be also provided selectively. In the embodiment, the functional fluid may be understood as a raw material which is included in cosmetic components for functional improvement, and particularly, a raw material which is legally approved with respect to functions. Further, the functional fluid may be also understood as meaning a fluid in which a functional raw material is dissolved or included.

Hereinafter, structure of the first container 210 will be described in detail. The other containers 220, 230, 240 may have the same structure, shape, size and function as the first container 210, so detailed description of the containers 220, 230, 240 will be omitted.

The first container 210 may include a storing part 212 storing a fluid therein, a pumping part 214 which is provided at one side of the storing part 212, and which performs a pumping action by being moved by the operative unit 30, an elastic member 215 which provides restoring force to the pumping part 214, a tube 211 which is provided inside the storing part 212 and connected to the pumping part 214, and through which a fluid can be intaken, and a discharging end 219 through which the fluid intaken through the tube 211 is discharged to the outside (see FIG. 4).

The storing part 212 provides a space S in which a fluid is stored, and may have such a three-dimension shape as to be inserted into the inside of the main body 120. The storing part 212 may be provided so as to be charged with fluid, and an opening for charging is provided by removing the pumping part 214, but may be formed by removing a lower part of the storing part.

In the storing part 212, a chamber 216 may be provided for providing a space whose volume is changed, so that the pumping action can take place. The volume of the chamber 216 may be changed by movement of the pumping part 214.

The pumping part 214 is a component which is pressed and moved by the operative unit 30 to produce pumping pressure, and may be provided, such that it can be moved inward and outward of the chamber 216 while changing the volume of the chamber 216.

The chamber 216 may be provided with a first valve 217 at one side, which selectively opens and closes an inner space of the chamber 216 to control the intake of the fluid through the tube 211, and a second valve 218 at the other side of the chamber 216, which selectively opens and closes an inner space of the chamber 216 to control the discharge of the fluid through the discharging end 219.

The tube 211 may be provided so as to extend from a point of the chamber 216 toward the bottom of the storing part 212, and sufficiently intake fluid stored in the storing part 212.

The discharging end 219 may be formed so as to extend to the chamber 216 penetrating through the pumping part 214, and may have a shape protruding from the pumping part 214 by a predetermined length for connection with a flow path 33 to be described later.

With such configuration, the container 210 may be operated as below. When the pumping part 214 is pressed down by being subjected to a force, the volume of the inner space of the chamber 216 is decreased, and the pressure of the inner space of the chamber 216 is increased. Due to such pressure change, the first valve 217 can operate so as to close a flow path, and the second valve 218 can operate so as to open a flow path, and thus the fluid stored in the inner space of the chamber 216 can be discharged through the discharging end 219. And, while the pumping part 214 is returned to its original position by action of the elastic member 215, the volume of the inner space of the chamber 216 is increased and the pressure of the inner space of the chamber is decreased. Due to this, the first valve 217 can operate so as to open the flow path, and the second valve 218 can operate so as to close the flow path, and thus the fluid of the storing space S can be introduced to the inner space of the chamber 216 through the tube 211. FIG. 4 may be understood as a schematic diagram for illustrating the above-mentioned operation.

The operation of the first container 210 may be performed by the movement of the operative unit 30, and the other containers 220, 230, 240 may be operated similarly.

Meanwhile, the discharging amounts of the first, second, third and fourth containers 210, 220, 230, 240 by the movement of the operative unit 30 may be set to be equal to each other. Herein, the discharging amount may be understood as an amount of fluid which is discharged from each container 210, 220, 230, 240 to the outside by a single press of each pumping part 214, 224, 234, 244. That is, the equal discharging amount of a container means that amounts of fluid discharged from each container 210, 220, 230, 240 to the outside by the single press of the operative unit 30 are equal to each other.

For example, the discharging amount of each container 210, 220, 230, 240 by the single press may be 0.01 cc to 0.1 cc. However, the discharging amount is not limited to this, and 0.1 cc or more may be discharged by a single press.

Further, discharging pressure of each container 210, 220, 230, 240 may be set to such a level that fluid can be discharged from the container 210, 220, 230, 240, pass through the channel unit 40 while being emulsified, and then can be discharged from the channel unit 40 to the outside. For example, the discharging pressure may be 1.5 kpa.

Meanwhile, the operative unit 30 may provide an external force required to form emulsion in the channel unit 40 and discharge the emulsion to the outside. In the embodiment, the operative unit 30 is described by way of example as being a pressing means of a plate form which receives and transfers force from the lid 110 to the containers 210, 220, 230, 240 to generate pressure for pumping. Technical idea of the invention is not limited to this, and the operative unit 30 may be provided with another mechanical mechanism or an electronic driving device.

Specifically, the operative unit 30 may be provided as a means which is disposed between the pumping parts 214, 224, 234, 244 of the containers 210, 220, 230, 240 and the channel unit 40 to be capable of pressing the pumping parts 214, 224, 234, 244. Herein, the operative unit 30 may serve as moving fluid discharged from the containers 210, 220, 230, 240 to the channel unit 40.

When the operative unit 30 is subjected to a downward force by a user pressing down the lid 110, the operative unit 30 can press the pumping parts 214, 224, 234, 244 of the containers 20. Specifically, the operative unit 30 may include a pressing surface 32 which contacts the pumping parts 214, 224, 234, 244. Herein, the pressing surface 32 may serve as a stopping part which determines an upper position of the container 20.

Further, the operative unit 30 may include a plurality of flow paths 33 through which fluid can be transferred from the container 20 to the channel unit 40. Each flow path 33 may be disposed so as to correspond to the position of each container 20, and may be penetratingly formed in an up and down direction to allow the fluid supplied from the below to move to the channel unit 40 at an upper side.

Further, the operative unit 30 may include a sliding surface 34 which slides along an inner surface of the main body 120, so that it can be moved along the inner surface of the main body 120 by an external force. The sliding surface 34 may be formed so as to surround the inside or outside of the main body 120, and an upper end inner surface of the main body 120 may serve as a guide surface.

The operative unit 30 may be elastically supported by the first elastic member 123a provided at a portion of the container main body 120. Further, at the neck part 122 of the container main body 120, a second elastic member 123b may be formed, which supports a portion of the operative unit 30. Specifically, a central portion of the operative unit 30 may be supported by the first elastic member 123a, and a circumferential portion of the operative unit 30 may be supported by the second elastic member 123b. Herein, elastic modulus of the first elastic member 123a may be greater than that of the second elastic member 123b. However, this is an example, and the elastic modulus of the second elastic member 123b may be greater than that of the first elastic modulus 123a.

Further, a force which restores the operative unit 30 to its original position may be provided by the elastic member 215 provided at the container 20.

The above-described operative unit 30 and the pumping parts provided at the containers 20 can produce pressure, and produce and discharge emulsion only with the mechanical construction without any electronic device. Therefore, the apparatus 1 for manufacturing cosmetic can be manufactured in such a small size as to be portable. Particularly, as each container 20 is separately provided with the pumping part, magnitude of pressure which the pumping part should provide can be minimized, and thus the pumping part can be realized with a minimum size, which in turn can lead to miniaturization of the apparatus 1 for manufacturing cosmetic using instantaneous emulsification.

Further, as the containers 20 may be provided in a replaceable manner, a user can selectively use the container 20 which stores a raw material that the user desires. Therefore, the user's satisfaction with the product can be increased.

Meanwhile, the fluid stored in the above-described container 20 may not include a surfactant.

Herein, the surfactant may be defined as a compound that has a hydrophilic portion which is likely to be dissolved in water, and a hydrophobic portion which is likely to be dissolved in oil, and that helps fluids, which are not easily mixed due to high surface tension of interfaces, to be mixed with each other. In the embodiment, the surfactant may be understood as an emulsifier.

Conventional cosmetics required surfactant in order to mix an internal phase fluid and an external phase fluid which are based on water and oil. However, according to an embodiment of the invention, there is provided the channel unit 40 which is capable of supplying emulsion by mixing and instantly emulsifying the internal phase fluid and the external phase fluid, and thus it is possible to produce emulsion without adding a surfactant. Specifically, the channel unit 40 is supplied with fluids from the plurality of containers 20 and can provide instantaneously emulsified emulsion.

Further, the channel unit 40 may be provided with introducing parts 402, 404, 406, 408 to which fluid is introduced from each container 210, 220, 230, 240. Herein, it is understood that the introducing parts 402, 404, 406, 408 may include one or more of an internal phase fluid injection hole 402, a first external phase fluid injection hole 404, a second external phase fluid injection hole 406, and a functional fluid injection hole 408, each of which will be described later. Further, in the embodiment, the first external phase fluid injection hole 404 and the second external phase fluid injection hole 408 are introducing holes through which the external phase fluid stored in the first container 210 and the fourth container 240 is introduced, and it is understood that they may be conceptually included in an external phase fluid injection hole. For example, in a case where only the first container 210 is provided as a container storing external phase fluid, the first external phase fluid injection hole 404 may be understood as the external phase fluid injection hole.

The channel unit 40 according to the embodiment provides a microfluidic channel formed in the channel unit 40, through which the internal phase fluid and the external phase fluid pass to be emulsified. The microfluidic channel of the channel unit 40 may be provided inside a plate 400, and the plate 400 may have a flat board shape. That is, the microfluidic channel of the channel unit 40 is disposed inside the plate 400 having a flat board shape, and thus the microfluidic channel can be located on the same plane inside the plate 400. As described above, the microfluidic channel is located on a single flat plate, and thus the apparatus for manufacturing cosmetic can be miniaturized.

For example, a cross section of the microfluidic channel (cross section of a flow path) formed inside the channel unit 40 may be a rectangular whose sides are 0.5 mm to 1 mm.

The cross section of the microfluidic channel (flow path) may be a circle whose diameter is 0.5 mm to 1 mm. As described above, when flow path inside the channel unit 40 is formed with the microfluidic channel, the flow speed of the fluid can increase, thus increasing the mixture of fluids and efficiency of emulsification. However, the cross section shape of the microfluidic channel is not limited to the shape described above.

According to the embodiment, the channel unit 40 may include an internal phase fluid injection hole 402 to which an internal phase fluid is supplied from the first container 210, a first external phase fluid injection hole 404 to which an external phase fluid is supplied from the second container 220, a confluence part 410 where the internal phase fluid supplied from the internal phase fluid injection hole 402 and the external phase fluid supplied from the first external phase fluid injection hole 404 are joined while emulsion particles are formed, a mixing section 420 which extends from the confluence part 410, and which includes a plurality of mixing parts 421, 422, 423, 424, 425 formed so as to generate vortices in flow by converting a proceeding direction of the fluid, and a particle size adjusting part 430 which makes uniform sizes of emulsion particles included in the fluid introduced from the mixing section 420.

Herein, the confluence part 410, the mixing section 420 and the particle size adjusting part 430, which are microfluidic channels, may be understood as a flow path extending by a predetermined length through which the fluid can move, and may be formed inside the plate 400. These microfluidic channels may serve as increasing the flow speed inside the channel in proportion to the reduction of cross section area, when a fluid is introduced into the channel unit 40 from the container 20. Further, by changing shapes of the microfluidic channels inside the plate 400 of a small surface area, it is possible to easily increase the contacting surface area or contacting time between two phases (internal phase fluid and external phase fluid). Further, the governing force of the surface tension in the microfluidic channel is much greater compared to macro environments.

Further, the channel unit 40 may include a first connecting flow path 403 which connects the internal phase fluid injection hole 402 with the confluence part 410, and a second connecting flow path 405 which connects the first external phase fluid injection hole 404 with the confluence part 410. In this case, an angle between the first connecting flow path 403 and the second connecting flow path 405 may be 80°-100°.

In a case where the internal phase fluid and the external phase fluid meet with each other in the confluence part 410 at the above-mentioned angle, a portion of the internal phase fluid may be broken before entering the mixing section 420. This may have a good effect on the formation of emulsion particles to contribute to the formation of emulsion.

Further, after the internal phase fluid and the external phase fluid have been mixed with each other in the confluence part 410, the mixture may be introduced into an initial flow path 429 of the mixing section 420.

For example, both an angle between the first connecting flow path 403 and the initial flow path 429 and an angle between the second connecting flow path 405 and the initial flow path 429 may be 135°.

Further, the channel unit 40 may include a functional fluid injection hole 408 to which a functional fluid is supplied from the third container 230, and a second external phase fluid injection hole 406 to which an external phase fluid is supplied from the fourth container 240. Further, the channel unit 40 may include a third connecting flow path 409 which connects the functional fluid injection hole 408 with the confluence part 410, and a fourth connecting flow path 407 which connects the second external phase fluid injection hole 406 with the confluence part 410. These configurations may be selectively provided according to whether the third container 230 or the fourth container 240 is provided or not.

An angle between the third connecting flow path 409 and the second connecting flow path 405 may be 80°-100°. Further, in a case where the functional fluid injection hole 408 is formed near the internal phase fluid injection hole 402, an angle between the third connecting flow path 409 and the first connecting flow path 403 may be 80°-100°.

Further, in a case where both the third container 230 storing a functional fluid, and the fourth container 240 storing another external phase fluid are provided, the first connecting flow path 403, the second connecting flow path 405, the third connecting flow path 409 and the fourth connecting flow path 407 may be disposed so as to form the same angle between themselves.

Meanwhile, in the embodiment, all the flow paths are described by way of example as being joined at one point, but according to an embodiment, confluence points of flow paths may be different from each other. That is, the confluence part 410 may be configured to have a plurality of confluence points.

Further, the plate 400 may be transparent, so that fluids can be seen flowing in the channel unit 40.

The mixing section 420 may include a plurality of the mixing portions 421, 422, 423, 424, 425, which extend from the confluence part 410, and which form vortices in flow by converting a proceeding direction of fluid.

The mixing parts 421, 422, 423, 424, 425 may be a flow path which can form vortices in flow by converting a proceeding direction of fluid, for example, a turning direction of fluid by a flow path. One mixing part may be understood as having one or more flow paths which covert a turning direction. For this, the mixing parts 421, 422, 423, 424, 425 may include a bent part, a curved part, a turning part and the like which can convert the proceeding direction of fluid. Particularly, in a case where the mixing parts 421, 422, 423, 424, 425 are formed so as to make fluid to turn one direction or both directions, the fluid is subjected to centrifugal force while vortices are being formed in the fluid, and thus the fluid can be mixed and emulsified at the same time while passing through the mixing parts 421, 422, 423, 424, 425.

Specifically, the vortices generated in the mixing parts 421, 422, 423, 424, 425 impart complex movements to the mixed fluids, and the movement of the external phase fluid governs the flow in the vortices as relatively more external phase fluid has been supplied. Such movements of the external phase fluid may be exerted on the internal phase fluid in such a manner as to make the flow of internal phase fluid thinner or break the flow of the internal phase fluid. Such exertions may be generated in each of all the mixing parts 421, 422, 423, 424, 425, and, in the channel unit 40 of a plate shape as in the embodiment, it is preferable to be subjected to three or more vortex generation sections in order to achieve emulsification to such an extent as to be suitable as cosmetics.

In the embodiment of the invention, there may be provided three or more mixing parts. In the embodiment of the invention, the mixing parts are described by way of example as being five in number (first mixing part 421, second mixing part 422, third mixing part 423, fourth mixing part 424, fifth mixing part 425). Herein, if the fluid has passed through the first to third mixing parts 421, 422, 423, it may be emulsified to such an extent as to be used as a cosmetic, and the fourth and fifth mixing parts 424, 425 may be used as an element which determines quality of formulation supplied to a user, by additionally emulsifying or mixing. That is, as necessary, the mixing part after the third mixing parts 423 may be selectively provided.

In the embodiment, the mixing parts 421, 422, 423, 424, 425 may be disposed on an outer circumference of the confluence part 410. In other words, when the plate constituting the channel unit 40 is viewed from the top, that is, when viewed from a viewpoint of FIG. 5, the mixing parts 421, 422, 423, 424, 425 may be arranged so as to surround the confluence part 410. That is, the mixing parts 421, 422, 423, 424, 425 may be disposed on a region between the confluence part 410 and the periphery of the plate 400. As described above, by arranging the mixing parts 421, 422, 423, 424, 425 on the region near the periphery of the plate 400, the length of the microfluidic channel of the mixing section 420 can be sufficiently elongated, and thus sufficient emulsification can be achieved even in a small-size plate. Thereby, the apparatus 1 for manufacturing cosmetic can be realized in a small size so as to be portable without burden.

The plurality of mixing parts 421, 422, 423, 424, 425 may be disposed in an order of the first mixing part 421, the second mixing part 422, the third mixing part 423, the fourth mixing part 424 and the fifth mixing part 425 from upstream connected with the confluence part 410 to downstream connected with the particle size adjusting part 430. Specifically, the mixing parts 421, 422, 423, 424, 425 may be generally arranged in a rotational manner in one direction (in the embodiment, a clockwise direction) with the confluence part 410 as a center. Herein, the first mixing part 421 and the third mixing part 423 may be disposed at opposite sides with respect to the confluence part 410, and the second mixing part 422 may connect the first mixing part 421 with the third mixing part 423, and be disposed at one side (right side in FIG. 5) of the confluence part 410. The fourth mixing part 424 and the fifth mixing part 425 may be arranged so as to be opposite to the second mixing part 422 with respect to the confluence part 410. Herein, the first to third mixing parts 421, 422, 423 may be arranged at the same distance from the confluence part 410.

While passing through the mixing part 420, the fluid can proceed from the first mixing part 421 to the fifth mixing part 425 to be subjected to emulsification.

Specifically, the internal phase fluid which has been mixed with the external phase fluid at the confluence part 410 may become thinner or be broken while passing through the first mixing part 421. Such progress can be repeated while passing through the downstream mixing parts 421, 422, 423, 424, 425, and finally emulsion can be formed in which fluid that has been broken into small pieces remains stably in the external phase fluid.

In the embodiment, the first mixing part 421 is described by way of example as being configured to rotate the entering fluid in one direction (in the embodiment, clockwise based on the drawing) and then rotate it in the other direction (in the embodiment, anticlockwise based on the drawing).

Specifically, the first mixing part 421 may include a first turning path 4211 which guides fluid so as to rotate in one direction, a second turning path 4212 which guides fluid so as to rotate in the other direction, and a direction conversion path 4213 which converts the rotating direction of the fluid between the first turning path 4211 and the second turning path 4212.

By this first mixing part 421, the internal phase fluid and the external phase fluid are moved along the first turning path 4211 and rotated in one direction, and the rotating direction is converted in the direction conversion path 4213 to be rotated in the other direction, so that vortices can be effectively generated. By the fluid force of the external phase fluid by vortices generated as described above, the internal phase fluid can be broken to be emulsified and mixed.

Further, the first mixing part 421 may include a vortex prompting path 4214 for prompting formation of vortices at upstream of the first turning path 4211 or downstream of the second turning path 4212. The vortex prompting path 4214 may be understood as imparting irregularity to fluid by turning the fluid which is flowing straightly, or by making the fluid, which is turning, flow straightly. Inclusion of such vortex prompting path 4214 can lead to the prompted formation of vortices and the easy generation of emulsion particles in the first mixing part 421. The second mixing part 422 to the fifth mixing part 424 may be formed with the same shape as that of the first mixing part, and the detailed description thereof will be omitted. FIG. 7 is a conceptual diagram for designing a vortex promoting path 4214.

Referring to FIG. 7, each end point of large semicircular lines, which can be formed by an imaginary straight line horizontally passing through the center of the mixing part 421, 422, 423, 424, 425, is connected to a curve. In this case, a length difference indicated by 'd' takes place. So, in order to remove such difference, the vortex prompting path 4214 is further formed, which in turn can lead to an effective utilization of space in the plate 400 of the channel unit.

Further, in the embodiment, the mixing parts 421, 422, 423, 424, 425 are described by way of example as being five in number on the channel unit 40, but the number and arrangement of the mixing parts do not limit the technical idea of the invention.

As described above, the vortices generated in the mixing parts 421, 422, 423, 424, 425 enable the internal phase fluid to be broken by the external phase fluid, thus forming emulsion particles. By continuously disposing these mixing parts 421, 422, 423, 424, 425, continuous emulsification can take place, which enables emulsion to be formed to such a level as to be suitably used as cosmetic even when the internal phase fluid and the external phase fluid do not contain any surfactant.

Further, the mixing section 420 may be disposed around the confluence part 410 and outside the injection holes 402, 404, 406, 408. This mixing section 420 can make fluid move along a longer path. That is, even when the surface area of the plate 400 is small, the mixing section 420 can be disposed such that the total surface area of the plate 400 can be utilized efficiently. For example, the length of the mixing section 420 may be greater than that of circumference of the plate 400.

Further, the microfluidic channel disposed inside the plate 400 may be spaced away from the outermost edge of the plate 400 by 5 mm or more. In this case, it is possible to more perfectly prevent leakage of emulsion caused by pressure of the microfluidic channel inside the plate 400.

Further, a minimum gap between microfluidic channels inside the plate 400 may be 1 mm or more. For example, the gap between adjacent microfluidic channels may be 1 mm or 2 mm.

The particle size adjusting part 430 is disposed at downstream of the mixing section 420. The particle size adjusting part 430 serves as forming fluid (emulsion) of uniform size, even though the fluid has been mixed at the mixing section 420 to have non-uniform sizes. The emulsion particles produced at the mixing parts 421, 422, 423, 424, 425 may have irregular sizes due to vortices which exhibit irregular movements, but their sizes can become uniform by means of the particle size adjusting part 430. Thereby, the emulsion which is finally prepared by the channel unit 40 can have a good quality and improved feeling of use.

The particle size adjusting part 430 may include a converging portion 431 in which the width W1 of a mixing flow path 426 of the mixing section 420 decreases, a convergence maintaining portion 432 which has a width W2 less than width W1 of the mixing flow path 426, a diverging portion 433 in which the width W2 of the convergence maintaining portion 432 increases, and a divergence maintaining portion 434 which has a width W3 greater than the width W1 of the mixing flow path 426.

Herein, a mean size of emulsion particles can be varied according to the width W2 of the convergence maintaining portion 432. That is, the smaller the width W2 of the convergence maintaining portion 432 is, the smaller the formed emulsion particles are. This particle size adjusting part 430 may be understood as being an orifice, and according to an embodiment, the converging portion 431 and the diverging portion 433 may be omitted.

Further, the mean size of emulsion particles may be adjusted by viscosity of fluid stored in each container 210, 220, 230, 240, cross sectional area of a channel, length of a channel, the width W2 of the particle size adjusting part 430 or the like.

Further, the width W2 of the convergence maintaining portion 432 of the particle size adjusting part 430 may be provided variously according to the size of emulsion particle to be set. For example, the width W2 of the convergence maintaining portion 432 of the particle size adjusting part 430 may be 0.1 mm to 0.5 mm.

Meanwhile, at downstream of the particle size adjusting part 430, there may be provided a discharging hole 455 through which emulsion is discharged from the channel unit 40.

A discharging part 456 which finally supplies emulsion to a user may be directly connected to the discharging hole 455. In the embodiment, the discharging part 456 may be directly connected to a lower side of the discharging hole 455, and for this, a portion of the plate constituting the channel unit 40 may be exposed to the outside.

The discharging part may form 90 degrees with the microfluidic channel formed in the plate. In this case, the movement direction of emulsion generated in the microfluidic channel formed inside the plate 400 may be changed abruptly when the emulsion moves from the discharging hole 455 to the discharging part 456. Therefore, flow speed of the emulsion moving from the microfluidic channel to the discharging part 456 can be decreased.

Further, distance between the discharging part 456 and the storing part 212 may correspond to ½ to ¼ size of a user's palm. For example, distance from the discharging part 456 to one side of the storing part 212 may be 10 mm to 70 mm. By having such distance, the user can receive the emulsion discharged from the lower side of the discharging part 456 and use it.

Further, length of the particle size adjusting part 430 may be correspondingly 10 mm to 70 mm.

Meanwhile, in the embodiment, the flow paths (microfluidic channels) formed in the channel unit 40 may substantially form a single layer path. The single layer path may be understood as a path in which height difference of flow paths is not involved in mixing and emulsification of each fluid or emulsification of the mixed fluid during the mixing and emulsification of fluid. The single layer path may correspond to the confluence part 410, the mixing section 420, the particle size adjusting part 430 or the like, which are realized on the single flat plate as in the embodiment. According to an embodiment, the plate constituting the channel unit 40 may be provided in plural, and a portion of flow path may be separated to be disposed on a different plate. Even in this case, each portion where mixing and emulsification of fluid take place may be realized on the same plate, and in general, may serve as a single layer path. For example, two plates may be stacked in an up and down direction, the confluence part 410 and the first to third mixing part 423 of the mixing section 420 may be formed in the lower layer pate, while the fourth mixing part 424, the particle size adjusting part 430 and the discharging hole 455 may be formed in the upper layer plate. However, in general they may form a series of flow paths, and the height difference may be prevented from being involved in the mixing and emulsification of fluid. In this case, although process unit prices may increase, planar surface area of the plates may be decreased, and thus the apparatus can be advantageously realized with a smaller size when mixing device and emulsifying device should be formed in a restricted space.

In the embodiment of the invention, the channel unit 40 and fluid (internal phase fluid and external phase fluid) may be provided such that Reynolds number Re is equal to or greater than 1, and preferably is equal to or greater than 10.

According to an embodiment, the internal phase fluid and the external phase fluid may have various ranges of viscosity. According to this, pressure which the channel unit 40 can endure may be determined, and for example, the channel unit 40 may be provided such that it can endure pressure of fluid having viscosity of 8000 cps.

Further, operation of the apparatus 1 for manufacturing cosmetic according to an embodiment of the invention will be described as below.

When a user exerts pressure to the lid 110 of the housing 10 or the plate 400 in which the channel unit 40 is formed, the plate 400 presses the operative unit 30 of each container 20 to introduce into the channel unit 40 the solution contained in each container 20.

The internal phase fluid, the external phase fluid and the functional fluid, which is selectively provided, have been introduced into the channel unit 40, and meet and mixed with each other at the confluence part 410. After that, the fluid which has been subjected to commencement of the mixing and emulsification at the confluence part 410 passes though the mixing section 420 while emulsification is performed and emulsification particles are mixed.

The fluid which has been mixed in the mixing section 420 passes through the particle size adjusting part 430 to make emulsion particles uniform. After that, the fluid is discharged to the outside through the discharging hole 455, which is the final path of the channel unit 40.

Further, in the embodiment, oil and water are described by way of example as being an internal phase fluid and an external phase fluid, but they are described as representative example of a hydrophobic fluid and a hydrophilic fluid, and any hydrophobic fluid and any hydrophilic fluid, which can form emulsion, may be used as an internal phase fluid and an external phase fluid.

Hereinafter, operation and effect of the apparatus 1 for manufacturing cosmetic as described above will be described.

FIG. 6 is a micrograph showing an emulsion particle of an emulsion composition manufactured using the apparatus for manufacturing cosmetic of FIG. 1.

Specifically, FIG. 6 is an experimental example of emulsion, which was generated by the apparatus 1 for manufacturing cosmetic according to the embodiment by using the first container 210 which stores an oil-based fluid that contains no surfactant, as oil that contains coloring matter in a weight ratio of 0.4%, and the second, third and fourth containers 220, 230, 240 which store water-based fluid that contains no surfactant.

Referring to FIG. 6, it can be confirmed that oil particles having a diameter of 1 mm to 2 mm were generated in a water-based fluid without any surfactant (O/W emulsion). As described above, according to an embodiment, the internal phase fluid and the external phase fluid can be emulsified by the channel unit 40 to generate emulsion without adding surfactant.

Further, since the mixing section 420 is arranged so as to efficiently utilize the total area of the plate 400, while making the length of the mixing section 420 longer, sufficient emulsification can be achieved even in a small-sized apparatus.

Further, by providing the particle size adjusting part 430 at the downstream of the mixing section 420, sizes of emulsion particles, which are discharged, can be made uniform and small, thus improving feeling of use.

Further, by using microfluidic channel in the channel unit 40, shapes of channels inside the narrow plate 400 can be variously changed, so that contact surface area between two phases (internal phase fluid and external phase fluid) can become larger, or contact time can be increased, thus facilitating the emulsification.

Further, the governing force of the surface tension in the channel unit 40 can become much greater, so that interphases of emulsion particles can be strong.

Further, in instantaneous emulsification system which employs the microfluidic channel of the channel unit 40, the time which it takes to form emulsion particles and actually use emulsion may be within a few seconds, and thus sufficient formulation stability can be achieved with a small amount of thickener or without thickener.

Further, an apparatus for manufacturing cosmetic according to an embodiment of the invention can form emulsion particles without surfactant by a user pressing a pump, and the manufactured formulation can reduce stimulus and risk of raw material precipitation caused by surfactant, and improve stickiness of surfactant.

Further, the plurality of containers 20 according to an embodiment of the invention are detachable to the housing 10, and the container 20 which contains fluid that a user want can be coupled to the housing 10 for use. That is, according to the number of the containers 20 and the kind of fluid contained in the container 20, the type of emulsion formed in the channel unit 40, i.e., O/W emulsion or W/O emulsion, can be determined.

Further, according to an embodiment of the invention, raw material stored in the container 20 can be used by being formed into a dosage in the channel unit 40, and thus customized cosmetic can be provided, which is capable of responding instantly.

Further, formulation of effective ingredient, feeling of use and content ratio are can be adjusted according to the kind of fluid contained in the container 20, and ratio of fluids discharged to the channel unit 40, and thus it is possible to manufacture customized cosmetics suitable for personal preference.

Further, by employing the independent pumping part 214, 224, 234, 244 to each container 210, 220, 230, 240, the amount (ratio of raw materials of cosmetic) of fluid discharged to the channel unit 40 according to the number of the containers 20 can be adjusted.

Hereinafter, embodiments of above-described apparatus for manufacturing cosmetic will be listed.

Item 1: An apparatus for manufacturing cosmetic, the apparatus comprising: a housing which forms an outer appearance; an internal phase container which is provided in the housing, and which stores internal phase fluid excluding surfactant; an external phase container which is provided in the housing, and which stores external phase fluid excluding surfactant; a channel unit which generates emulsion by mixing the internal phase fluid provided from the internal phase container and the external phase fluid provided from the external phase container; and an operative unit which provides external force required to form and discharge emulsion at the channel unit by manipulation of a user, wherein by operation of the operative unit, more amount of the external phase fluid is supplied to the channel unit than the internal phase fluid, and wherein the channel unit includes: an internal phase fluid injection hole to which the internal phase fluid is provided from the internal phase container; an external phase fluid injection hole to which the external phase fluid is provided from the external phase container; a confluence part in which the internal phase fluid provided from the internal phase fluid injection hole and the external phase fluid provided from the external phase fluid injection hole are mixed with each other; and a mixing section including a plurality of mixing parts which extend from the confluence part, and which generate emulsion particles by converting proceeding direction of fluid and thus forming vortices in flow.

Item 2: An apparatus for manufacturing cosmetic of Item 1, wherein the respective internal phase container and the external phase container are provided one or more in number, and the channel unit is provided with introducing parts to which fluids from the internal phase container and the external phase container flow, and wherein the fluids which have flown to the introducing parts are guided to the confluence part to be mixed with each other.

Item 3: An apparatus for manufacturing cosmetic of Items 1 and 2, wherein by one-time operation of the operative unit, total discharging amount of the external phase fluid discharged from the external phase container is greater than total discharging amount of the internal phase fluid discharged from the internal phase container.

Item 4: An apparatus for manufacturing cosmetic of Items 1 to 3, the apparatus further comprising: a functional container which is provided in the housing, and which stores functional fluid, wherein the channel unit includes a functional fluid injection hole to which the functional fluid is introduced from the functional container, and the functional fluid which has flown to the functional fluid injection hole is guided to the confluence part to be mixed with the internal phase fluid and the external phase fluid.

Item 5: Apparatus for manufacturing cosmetic of Items 1 to 4, wherein the plurality of mixing parts is disposed around the confluence part with the confluence part as a center.

Item 6: An apparatus for manufacturing cosmetic of Items 1 to 5, wherein the channel unit is formed in one or more plates, and the confluence part and the mixing section are provided in a continuous single layer path.

Item 7: An apparatus for manufacturing cosmetic of Items 1 to 6, wherein the channel unit is formed in the plate of a single planar panel shape, and the confluence part and the mixing section are located on same planar surface in the plate.

Item 8: An apparatus for manufacturing cosmetic of Items 1 to 7, wherein the mixing part includes: a first turning path which guides an entering fluid to be rotated in one direction; a second turning path which guides the fluid rotating in one direction to be rotated in another direction; and a direction converting path which changes a rotational direction of fluid between the first turning path and the second turning path.

Item 9: An apparatus for manufacturing cosmetic of Items 1 to 8, wherein the mixing part further includes a vortex prompting path for prompting formation of vortices at upstream of the first turning path or downstream of the second turning path.

Item 10: An apparatus for manufacturing cosmetic of Items 1 to 9, wherein the mixing part is provided three or more in number.

Item 11: An apparatus for manufacturing cosmetic of Items 1 to 10, wherein the mixing section includes: a first mixing part which is connected to the confluence part; a third mixing part which is located opposite to the first mixing part with respect to the confluence part; and a second mixing part which is located between the first mixing part and the third mixing part.

Item 12: An apparatus for manufacturing cosmetic of Items 1 to 11, wherein the mixing section includes a fourth mixing part and a fifth mixing part which are located opposite to the second mixing part with respect to an imaginary straight line passing through the first mixing part, the third mixing part and the confluence part.

Item 13: An apparatus for manufacturing cosmetic of Items 1 to 12, wherein the channel unit further includes a particle size adjusting part which reduces size of the emulsion particle included in fluid provided from the mixing section.

Item 14: An apparatus for manufacturing cosmetic of Items 1 to 13, wherein the particle size adjusting part includes a convergence maintaining portion which has a width less than that of the mixing flow path of the mixing section.

Item 15: An apparatus for manufacturing cosmetic of Items 1 to 14, wherein the particle size adjusting part includes a divergence maintaining portion which is disposed at a rear end of the convergence maintaining portion, and which has a width greater than that of the mixing flow path of the mixing section.

Item 16: An apparatus for manufacturing cosmetic of Items 1 to 15, wherein the discharging part which discharges the emulsion is directly connected to a discharging hole formed in the channel unit.

What is claimed is:

1. An apparatus for manufacturing cosmetic, the apparatus comprising:
    a housing which forms an outer appearance;
    an internal phase container which is provided in the housing, and which stores internal phase fluid excluding surfactant;
    an external phase container which is provided in the housing, and which stores external phase fluid excluding surfactant;
    a channel unit which generates emulsion by mixing the internal phase fluid provided from the internal phase container and the external phase fluid provided from the external phase container; and
    an operative unit which provides external force required to form and discharge emulsion at the channel unit by manipulation of a user,
    wherein by operation of the operative unit, more amount of the external phase fluid is supplied to the channel unit than the internal phase fluid, and
    wherein the channel unit includes:

an internal phase fluid injection hole to which the internal phase fluid is provided from the internal phase container;

an external phase fluid injection hole to which the external phase fluid is provided from the external phase container;

a confluence part in which the internal phase fluid provided from the internal phase fluid injection hole and the external phase fluid provided from the external phase fluid injection hole are mixed with each other; and a mixing section including a plurality of mixing parts which extend from the confluence part, and which generate emulsion particles by converting proceeding direction of fluid and thus forming vortices in flow.

2. The apparatus for manufacturing cosmetic of claim 1, wherein the respective internal phase container and the external phase container are provided one or more in number, and the channel unit is provided with introducing parts to which fluids from the internal phase container and the external phase container flow, and wherein the fluids which have flown to the introducing parts are guided to the confluence part to be mixed with each other.

3. The apparatus for manufacturing cosmetic of claim 1, wherein by one-time operation of the operative unit, total discharging amount of the external phase fluid discharged from the external phase container is greater than total discharging amount of the internal phase fluid discharged from the internal phase container.

4. The apparatus for manufacturing cosmetic of claim 1, the apparatus further comprising:

a functional container which is provided in the housing, and which stores functional fluid, wherein the channel unit includes a functional fluid injection hole to which the functional fluid is introduced from the functional container, and the functional fluid which has flown to the functional fluid injection hole is guided to the confluence part to be mixed with the internal phase fluid and the external phase fluid.

5. The apparatus for manufacturing cosmetic of claim 1, wherein the plurality of mixing parts is disposed around the confluence part with the confluence part as a center.

6. The apparatus for manufacturing cosmetic of claim 1, wherein the channel unit is formed in one or more plates, and the confluence part and the mixing section are provided in a continuous single layer path.

7. The apparatus for manufacturing cosmetic of claim 1, wherein the channel unit is formed in the plate of a single planar panel shape, and the confluence part and the mixing section are located on same planar surface in the plate.

8. The apparatus for manufacturing cosmetic of claim 1, wherein the mixing part includes:

a first turning path which guides an entering fluid to be rotated in one direction;

a second turning path which guides the fluid rotating in one direction to be rotated in another direction; and a direction converting path which changes a rotational direction of fluid between the first turning path and the second turning path.

9. The apparatus for manufacturing cosmetic of claim 8, wherein the mixing part further includes a vortex prompting path for prompting formation of vortices at upstream of the first turning path or downstream of the second turning path.

10. The apparatus for manufacturing cosmetic of claim 1, wherein the mixing part is provided three or more in number.

11. The apparatus for manufacturing cosmetic of claim 1, wherein the mixing section includes:

a first mixing part which is connected to the confluence part;

a third mixing part which is located opposite to the first mixing part with respect to the confluence part; and a second mixing part which is located between the first mixing part and the third mixing part.

12. The apparatus for manufacturing cosmetic of claim 11, wherein the mixing section includes a fourth mixing part and a fifth mixing part which are located opposite to the second mixing part with respect to an imaginary straight line passing through the first mixing part, the third mixing part and the confluence part.

13. The apparatus for manufacturing cosmetic of claim 1, wherein the channel unit further includes a particle size adjusting part which reduces size of the emulsion particle included in fluid provided from the mixing section.

14. The apparatus for manufacturing cosmetic of claim 13, wherein the particle size adjusting part includes a convergence maintaining portion which has a width less than that of the mixing flow path of the mixing section.

15. The apparatus for manufacturing cosmetic of claim 14, wherein the particle size adjusting part includes a divergence maintaining portion which is disposed at a rear end of the convergence maintaining portion, and which has a width greater than that of the mixing flow path of the mixing section.

16. The apparatus for manufacturing cosmetic of claim 1, wherein the discharging part which discharges the emulsion is directly connected to a discharging hole formed in the channel unit.

* * * * *